United States Patent [19]

Gibboney et al.

[11] Patent Number: 5,644,070

[45] Date of Patent: Jul. 1, 1997

[54] OZONE CONCENTRATION SENSOR

[75] Inventors: Dennis A. Gibboney, Mt. Pleasant; Paul A. Bauer, Jr., Pittsburgh, both of Pa.

[73] Assignee: Dynamic Manufacturing Inc., Pittsburgh, Pa.

[21] Appl. No.: 636,159

[22] Filed: Apr. 22, 1996

[51] Int. Cl.$^6$ .......................... G01N 29/18; C01B 13/10; A61L 9/00
[52] U.S. Cl. .................. 73/23.2; 73/23.32; 73/31.01; 73/24.01; 422/186.08; 422/83
[58] Field of Search .................. 73/23.2, 23.32, 73/31.01, 31.02, 24.01; 422/186.08, 186.12, 83

[56] References Cited

U.S. PATENT DOCUMENTS

| | | | |
|---|---|---|---|
| 4,051,045 | 9/1977 | Yamamoto et al. | 250/536 |
| 4,128,768 | 12/1978 | Yamamoto et al. | 250/535 |
| 4,138,724 | 2/1979 | Kawauchi | 364/500 |
| 4,314,344 | 2/1982 | Johns et al. | 364/500 |
| 5,184,500 | 2/1993 | Krema et al. | 73/23.2 |
| 5,223,105 | 6/1993 | Arthurson | 204/176 |
| 5,247,826 | 9/1993 | Frola et al. | 73/24.01 |
| 5,285,675 | 2/1994 | Colgate et al. | 73/23.2 |
| 5,368,816 | 11/1994 | Detzer | 422/28 |
| 5,402,665 | 4/1995 | Hart et al. | 73/16 |
| 5,403,441 | 4/1995 | McDonald | 162/38 |
| 5,443,800 | 8/1995 | Dunder | 422/186.16 |
| 5,467,637 | 11/1995 | Hasegawa et al. | 73/24.01 |
| 5,540,898 | 7/1996 | Davidson | 422/186.15 |

*Primary Examiner*—Hezron E. Williams
*Assistant Examiner*—J. David Wiggins
*Attorney, Agent, or Firm*—MacMillan, Sobanski & Todd

[57] ABSTRACT

An ozone concentration sensor for use with an ozone generator. The ozone free feed gas to the ozone generator is briefly fed to the sensor which measures both the temperature of the feed gas and the time it takes a high frequency sound pulse to travel a predetermined distance in the feed gas for reference date. A portion of the output gas from the ozone generator is then fed to the sensor and the same measurements are made for the output gas. A programmed microcomputer determines the ozone concentration in the output gas from the measurements. In one embodiment, the sensor constantly receives output gas from the ozone generator. The reference measurements are made while operation of the ozone generator is briefly interrupted and feed gas passes through the ozone generator unchanged. Reference measurements may be stored and used for repeated ozone concentration calculations, so long as there is no significant change in the feed gas.

9 Claims, 5 Drawing Sheets

OZONE CONCENTRATION SENSOR

TECHNICAL FIELD

The invention relates to gas concentration measurement and more particularly to a sensor for accurately measuring the concentration of ozone in the output gas from an ozone generator.

BACKGROUND ART

Ozone is used for various industrial applications, for example, as an oxidizing agent and as a bactericide. One major application for ozone is in purifying potable water. Another application is in the treatment of sewage. Still another exemplary application is to oxidize volatile organic compounds (VOC's) in air. In addition to industrial applications, ozone has been used for treating residential swimming pools to reduce the need for chemicals such as chlorine and has been used for medical purposes. Ozone also has been used to treat pond water, for example, in zoo ponds for hippos and in fish farm ponds.

One type of ozone generator uses high voltage corona discharges to convert a portion of the oxygen in a feed gas to ozone. Another type of ozone generator uses high intensity light to convert oxygen to ozone. Either air or, preferably, a gas containing a high concentration of oxygen is fed to the ozone generator and a portion of the oxygen in the feed gas is converted to ozone. A high concentration oxygen output from an oxygen concentrator, for example, may be used to supply the feed gas for an ozone generator. An oxygen concentrator removes nitrogen from air and typically produces about 92% to 95% pure oxygen, with the remainder being primarily argon. When air is used as the feed gas, a typical ozone generator may produce a gas having up to about 1% ozone concentration. When 92% to 95% concentration oxygen from an oxygen concentrator is used as the feed gas, a typical ozone generator may produce up to about 5% ozone concentration. With an extremely high efficiency ozone generator, the output may have up to about 20% ozone concentration. However, the amount of ozone in the output from an ozone generator may decrease over a period of time, primarily due to a declining efficiency of the oxygen concentrator in providing a constant feed stock.

It should be appreciated that when air or an oxygen rich gas is supplied to an ozone generator, the same quantity of gas will be discharged from the ozone generator, whether or not the ozone generator is working properly. It is often desirable to know if the ozone generator is working properly, especially when the ozone is used for purification of potable waters. In order to monitor the composition of the output gas from an ozone generator, it is necessary to have an ozone monitor or ozone level sensor. In the past, only a few ozone monitors have been available and they have tended to be expensive and inaccurate.

It is known in the art that the concentration of oxygen in gas can be determined from the temperature of the gas and the speed that a high frequency sound pulse travels through the gas. U.S. Pat. No. 5,247,826 discloses a gas concentration sensor in which two piezoelectric transducers are connected together through a coiled tube. Oxygen containing gas from an oxygen concentrator, for example, is passed over one transducer, through the tube and over the other transducer. A thermistor is located at the center of the tube for measuring the average temperature of the gas as it flows through the tube. Periodically, one of the transducers is pulsed and the time required for a sound wave to travel to the other transducer is measured. It will be appreciated that the time will be influenced by the direction that the pulse travels relative to the direction of the gas flow through the tube. In order to eliminate the influence of the gas flow, the two transducers are alternately used for sending and receiving pulses. The pulse travel times both in the direction of the gas flow and against the gas flow are used to determine the oxygen concentration. The coiled tube is used between the transducers to increase the time that it takes for a sound pulse to travel between the transducers, thus increasing the accuracy of the measurement. A direct reading approach is used for determining oxygen level. In other words, the output of the oxygen concentrator is not compared with a reference gas having a known oxygen level. The gas concentration sensor disclosed in this patent has not been used for measuring the concentration of ozone from an ozone generator.

DISCLOSURE OF INVENTION

The invention is directed to a highly accurate and relatively inexpensive sensor for measuring the concentration of ozone produced by an ozone generator. It is known that the speed that a high frequency sound pulse travels through a gas is a function of the composition and of the temperature of the gas. If only the ratio between two gases in two gaseous mixtures and the temperature of the mixtures change, and all other conditions remain unchanged, it has been found that the change in the concentration of the gases may be accurately determined from the temperatures and the change in the speed of a high frequency sound pulse through the gases before and after the gas composition change.

According to the invention, a sensor is provided which is capable of passing high frequency sound pulses through gas and of measuring the sound pulse travel time over a predetermined distance. The sensor also measures the temperature of the gas. The measured time and temperature inputs are supplied to a programmed microcomputer. In operation, the sensor is positioned to receive gas discharged from the output of an ozone generator. Initially, the essentially ozone free feed gas for the ozone generator is delivered to the ozone sensor for a sufficient time to purge ozone containing gas from the ozone sensor. After all ozone containing gas is purged from the sensor, a pulse travel time and the gas temperature are measured to obtain base information for the feed gas. Since ozone is an unstable gas, it is not normally present in the feed gas in any significant quantity. After the feed gas pulse travel time and gas temperature readings are taken, ozone enriched output gas from the ozone generator is passed through the ozone sensor and the temperature and pulse travel time are measured for the ozone containing output gas. The microcomputer then calculates the ozone concentration in the output gas from the two temperature measurements and the two pulse travel time measurements.

In one embodiment of the invention, the ozone sensor continuously receives a flow of output gas from the ozone generator. Reference pulse speed and temperature data on the feed gas is taken by briefly interrupting operation of the ozone generator. While the ozone generator is off, the output gas flowing to the sensor will have the same composition as the feed gas. An optional accumulator may be used to provide a constant flow of ozone enriched gas while the ozone generator is briefly turned off. In a modified embodiment of the invention, the ozone generator remains on at all times. Valves are provided for selectively delivering either the feed gas or the ozone containing gas to the sensor.

Accordingly, it is an object of the invention to provide an improved ozone concentration sensor for use with an ozone generator.

Other objects and advantages of the invention will become apparent from the following detailed description of the invention and the accompanying drawings.

BEST MODE FOR CARRYING OUT THE INVENTION

Figure 1:
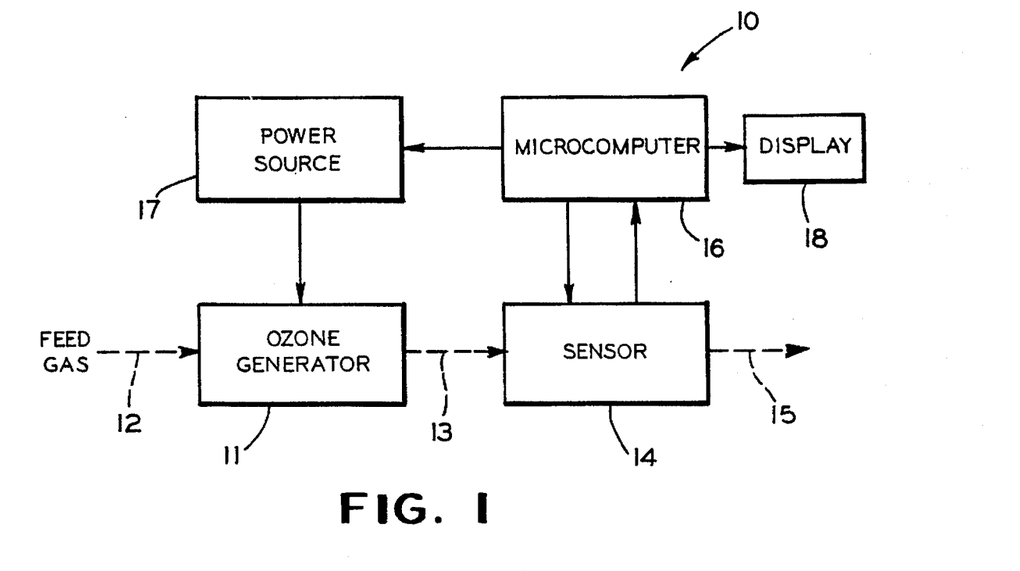
FIG. 1 is a schematic block diagram of an ozone system having an ozone concentration sensor connected to an ozone generator according to a first embodiment of the invention.

Referring to FIG. 1 of the drawings, an ozone system 10 is illustrated in diagrammatic form. The ozone system 10 is designed for use with a conventional ozone generator 11. The ozone generator 11 receives a feed gas 12 from a suitable source (not shown), such as an oxygen concentrator which supplies a flow of oxygen rich gas or a blower which supplies a flow of pressurized air. The gas flow path is shown as dashed lines in the drawings. Air typically has about 19% oxygen, about 1% argon and about 80% nitrogen. Commercially available oxygen concentrators use a molecular sieve to separate nitrogen from air, leaving a gas typically having a composition of about 92% to 95% oxygen and about 5% argon. A typical ozone generator 11 has an output gas flow 13 which is on the order of about 1% to 5% ozone. The actual ozone concentration in the output gas 13 will depend on the oxygen concentration in the feed gas 12 and on the efficiency of the ozone generator 11. The ozone is converted from oxygen in the feed gas 12 and all other constituents of the output gas 13 remain the same as in the feed gas 12. The output gas 13 is passed through a sensor 14. The gas exits the sensor 14 as a flow 15 which may be used for any desired purpose.

A programmed microcomputer 16 is connected to the sensor 14 and either to a power source 17 which operates the ozone generator 11, as shown, or directly to the ozone generator 11. The microcomputer 16 controls the operation of the sensor 14 and receives data from the sensor 14 which it uses to determine the ozone concentration in the output gas 13. Periodically, the microcomputer 16 shuts off the ozone generator power source 17 to interrupt the generation of ozone. While the ozone generator 11 is off, the output gas 13 will have the same composition as the ozone free feed gas 12. After all ozone is purged from the sensor 14, the microcomputer 16 reads and stores measurements corresponding to the temperature of the gas and to the speed that a sound wave travels over a predetermined distance in the gas. The microcomputer 16 then turns on the ozone generator 11 and once the output gas flow 13 has stabilized, similar temperature and sound speed measurements are taken and stored for the ozone containing output gas 13. As will be described in greater detail below, the microcomputer 16 is programmed to determine the ozone concentration from the stored measurements. Once the ozone concentration in the output gas flow 13 is determined, it may be delivered to a display 18 and/or it may be used by, for example, a controller (not shown) for a process which uses the ozone.

Figure 2:
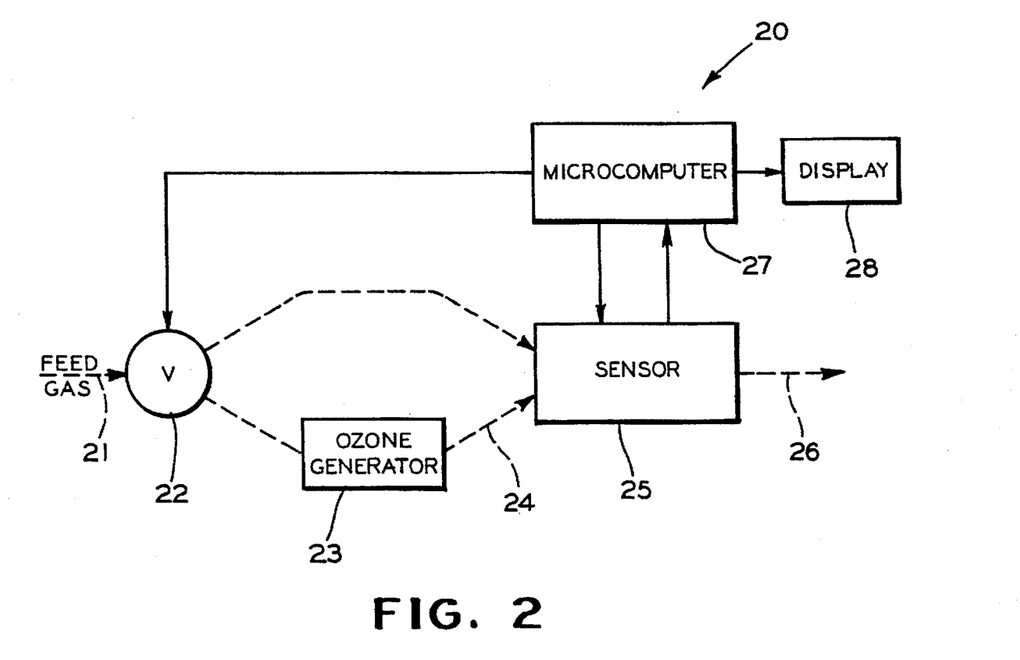
FIG. 2 is a schematic block diagram of an ozone system according to a second embodiment of the invention.

FIG. 2 illustrates a modified embodiment of an ozone system 20. Feed gas 21 containing oxygen is normally delivered through a valve 22 to an ozone generator 23. Output gas 24 from the ozone generator 23 is passed through a sensor 25 and exits as a output flow 26. The valve 22 may be actuated to deliver the feed gas flow 21 directly to the sensor 25. A microcomputer 27 is connected to control the valve 22 and the sensor 25 and to receive gas measurement data from the sensor 25. Measurements are made by the sensor 25 of both the temperatures and the speeds of high frequency sound pulses in the feed gas 21 and in the ozone containing output gas 24 and the microcomputer 27 is programmed to use this data for calculating the ozone concentration. The ozone concentration calculated by the microcomputer 27 may be shown on a display 28 or may be used in controlling a process in which the ozone containing exit gas flow 26 is used. If desired, the exit gas flow 26 may be passed through an optional accumulator (not shown) to reduce fluctuations in the concentration of the output gas from the sensor 25 while the feed gas is briefly passed through the sensor 25.

Figure 3:
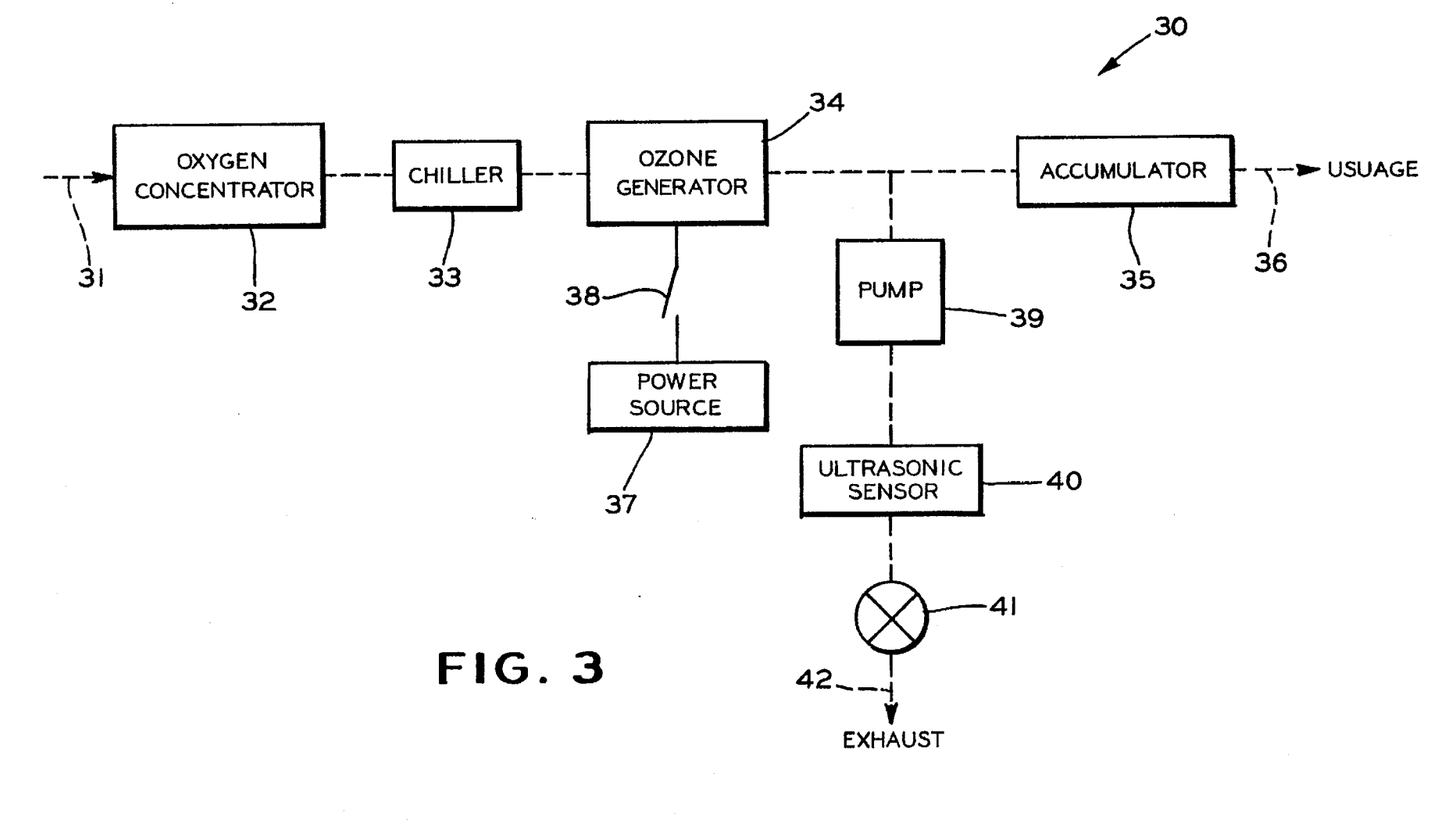
FIG. 3 is a schematic block diagram of an ozone system according to a third embodiment of the invention.

The ozone system 20 of FIG. 2 has a disadvantage in that the ozone flow is interrupted while reference data is taken on the feed gas. FIG. 3 illustrates an embodiment of an ozone system 30 which provides a continuous flow of ozone. A flow of feed gas 31, such as ambient air, is drawn into an oxygen concentrator 32. The oxygen enriched output from the oxygen concentrator 32 is passed through a chiller 33 to an ozone generator 34. The chiller 33 is optional and is provided to increase the efficiency of the ozone generator 34. From the ozone generator 34, the ozone enriched gas passes to an optional accumulator tank 35 and then to an exit conduit 36 for usage. A power supply 37 is connected through a normally closed switch 38 for operating the ozone generator 34. The ozone enriched gas from the ozone generator 34 is also supplied through a pump 39 which delivers a continuous flow through a sensor 40 and then through either a back pressure control valve 41 or a flow restrictor to an exhaust 42.

In operation, a microcomputer controller (not shown) controls operation of the sensor 40 and of the switch 38. Most of the output gas flow from the ozone generator 34 flows to the accumulator tank 35 for use, while a small portion of the output gas is passed through the sensor 40 and is exhausted into the atmosphere. Periodically, the switch 38 is opened by the controller to interrupt ozone production for a sufficient time to purge ozone from the sensor 40 and to obtain reference readings on the ozone free feed gas. The switch 38 is then closed to reestablish ozone production and readings are taken for the ozone enriched gas. The accumulator 35 holds a sufficient volume of gas to provide a continuous flow of ozone enriched gas. The switch 38 may be opened to interrupt ozone generation for a brief period of time, such as about 10 to 15 seconds every 5 to 10 minutes. The optional accumulator tank 35 prevents the ozone usage stream from ever dropping significantly in ozone concentration. For example, an ozone generator 34 capable of creating a 5% ozone concentration output would have an accumulator average output of about 4.85% ozone if an interrupted cycle of 10 seconds off to 5 minutes on is used. Moreover, with an appropriate accumulator tank volume, little fluctuation in ozone output will occur during the on/off periods. Thus, the ozone system 30 is suitable for applications which cannot accommodate interruption in ozone output.

Figure 4:
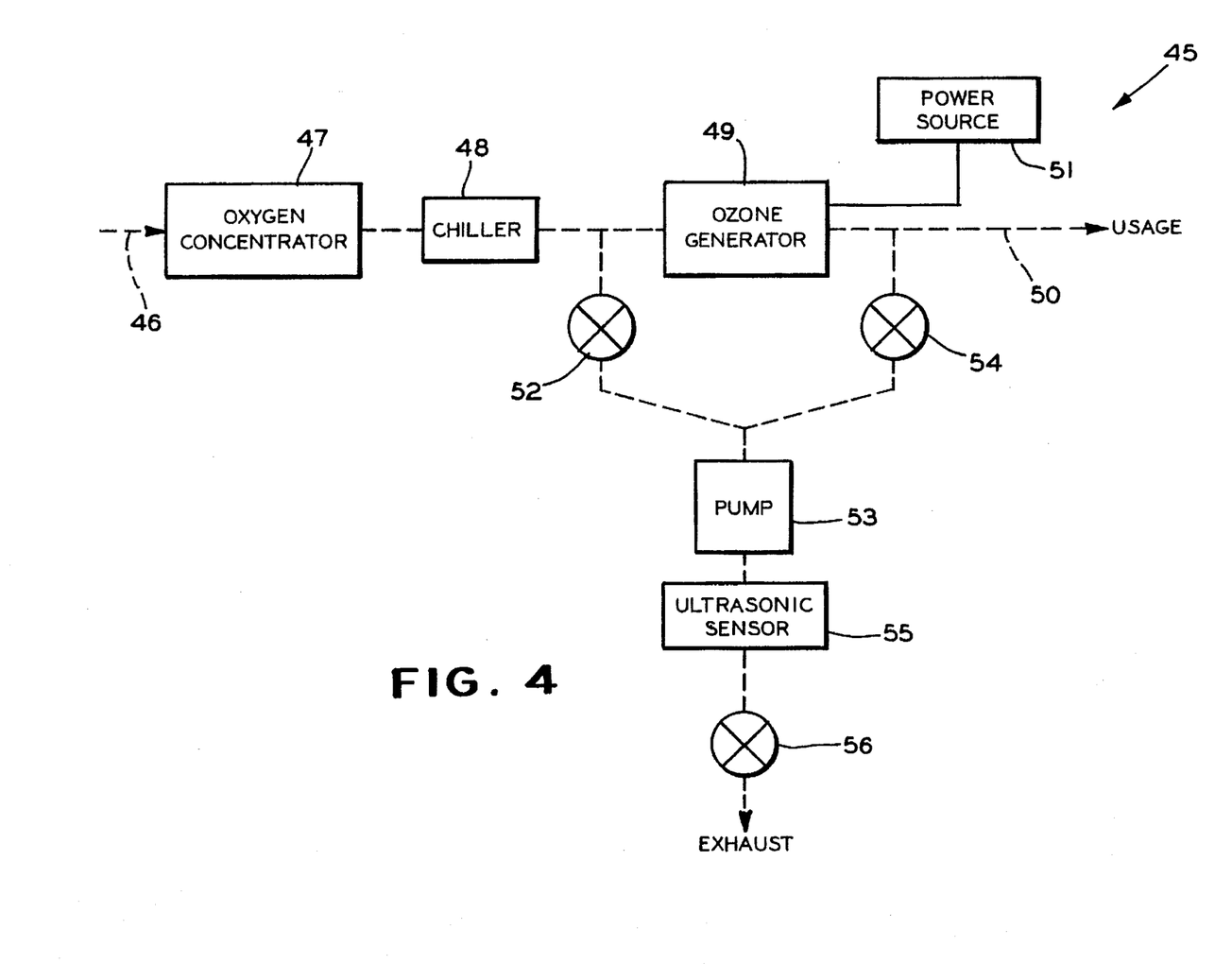
FIG. 4 is a schematic block diagram of an system according to a fourth embodiment of the invention.

FIG. 4 shows still another embodiment of an ozone system 45 according to the invention. A flow 46 of air or other feed gas passes through an oxygen concentrator 47 and the oxygen enriched output gas is passed through an optional chiller 48 to an ozone generator 49. The ozone generator 49 has a continuous ozone enriched output 50 which is utilized in any desired process. The ozone generator 49 is operated from a power supply 51 which is not interrupted, as in the above described system 30. A valve 52 is connected to receive oxygen enriched gas from between the chiller 48 and the ozone generator 49 and to deliver such gas to an inlet to a pump 53. A second valve 54 is connected to deliver ozone enriched output gas from the ozone generator output 50 to the inlet of the pump 53. An outlet from the pump 53 is passed through a sensor 55 and a flow restrictor or back pressure control valve 56 and is then exhausted to atmosphere. In operation, a microcomputer controller (not shown) initially closes the valve 54 and opens the valve 52 to allow the oxygen enriched feed gas from the ozone generator 49 to pass through the sensor 55. After a brief reading is taken for the oxygen enriched gas, the valve 52 is closed and the valve 54 is opened to allow the ozone enriched gas to flow through the sensor 55. If desired for environmental reasons, the valve 54 or a separate valve may be adapted to return the exhaust from the back pressure control valve to the output 50 when ozone enriched gas is passed through the sensor 55.

Figure 5:
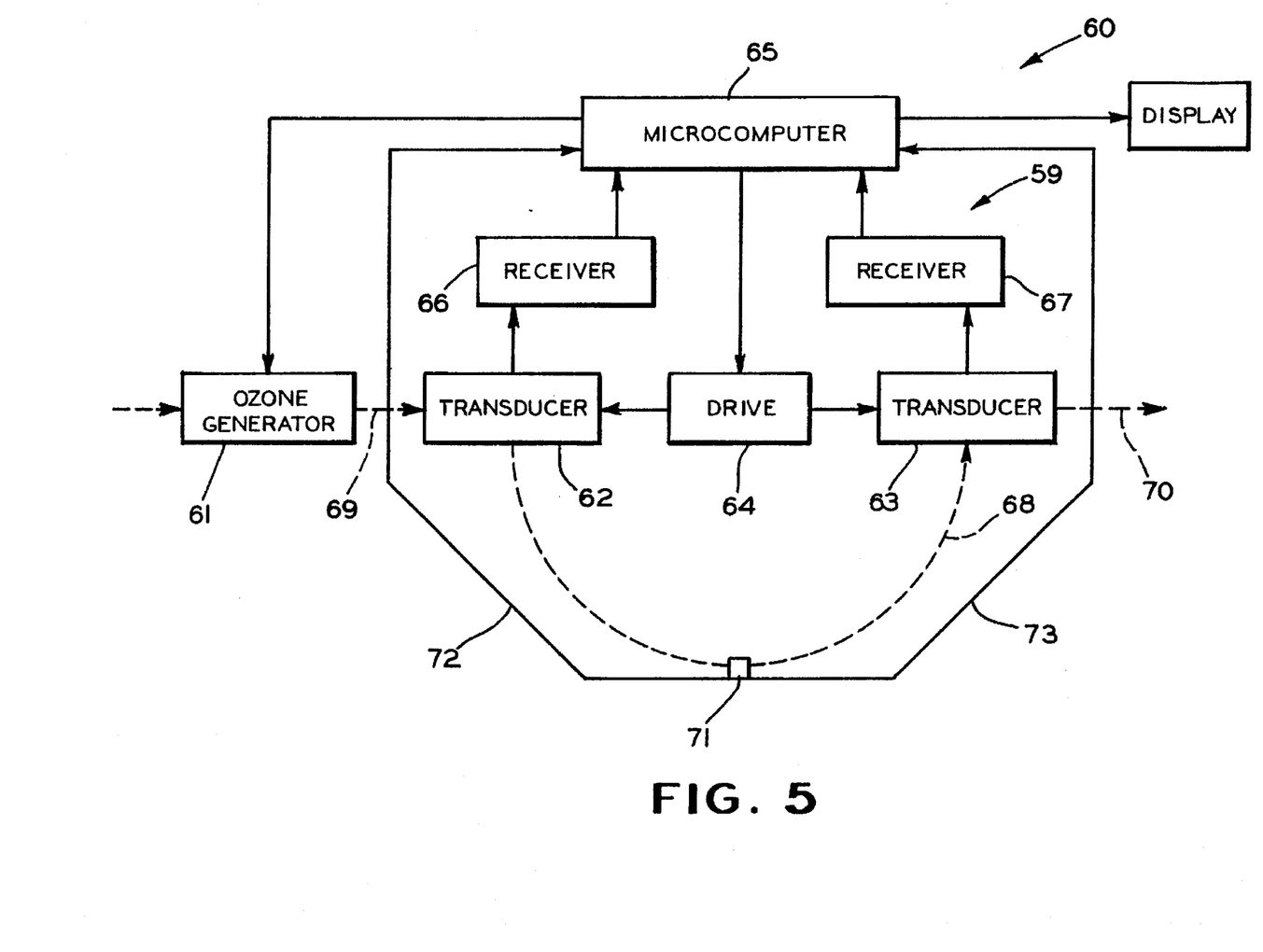
FIG. 5 is a more detailed schematic block diagram of an ozone concentration sensor according to the invention.
Figure 6:
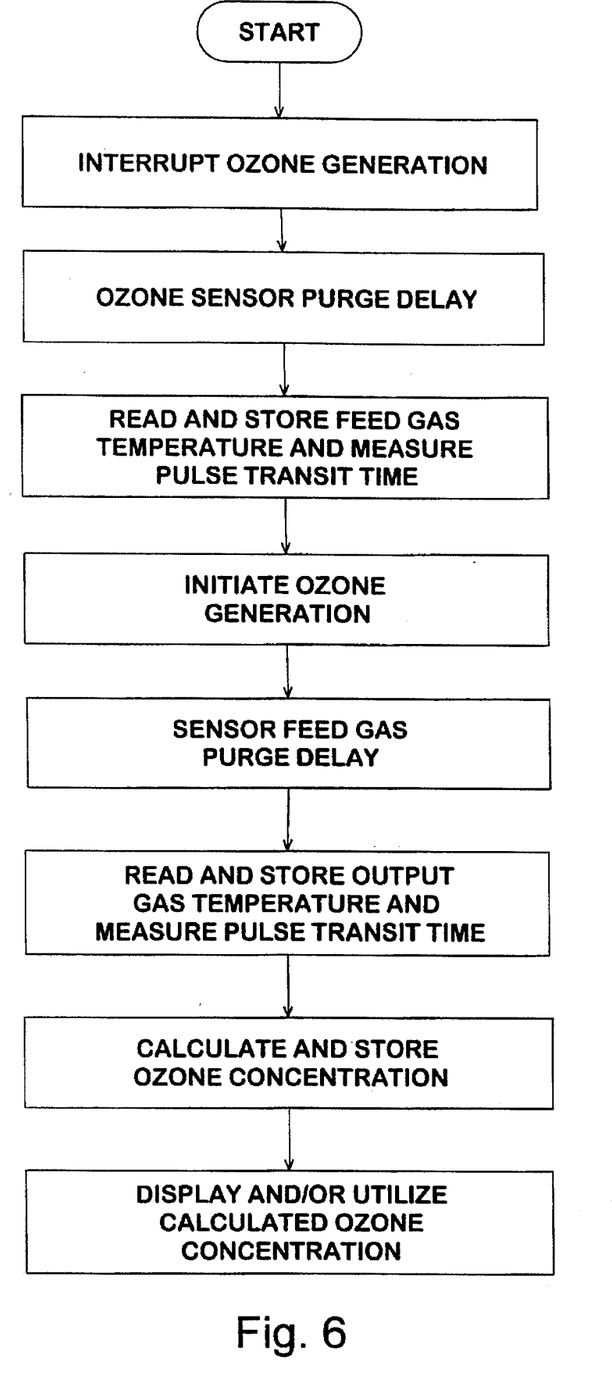
FIG. 6 is a flow chart illustrating the operation of the ozone concentration sensor of the invention.

The ozone sensors 14, 25, 40 and 55 may be of a construction similar to that shown in U.S. Pat. No. 5,247, 826, and the disclosure of such patent is incorporated herein. The adaptation of a sensor 59 to an ozone system 60 is illustrated in FIG. 5 and the operation of the system 60 for determining ozone concentration from the ozone generator 61 is illustrated in the flow chart of FIG. 6. The sensor 59 includes two transducers 62 and 63 which may be, for example, piezoelectric transducers. Such transducers produce a mechanical movement when excited by an electrical pulse and produce an electric signal when mechanically excited. Thus, the transducers are capable of acting both as a sound pulse transmitter and as a sound pulse receiver.

A drive circuit 64 is connected to selectively pulse the transducers 62 and 63 in response to commands from a microcomputer 65. The transducer 62 also is connected through a receiver circuit 66 to the microcomputer 65 and the transducer 63 is connected through a receiver circuit 67 to the microcomputer 65. The transducers 62 and 63 are connected together through a gas flow path 68. The flow path 68 may be a straight line path in a housing or may extend through a coiled tube in order to create a longer flow path than the physical distance between the transducers 62 and 63. An output gas flow 69 from the ozone generator 61 flows past the transducer 62 along the flow path 68 to the transducer 63 to the exit gas flow 70. A temperature sensor 71 is located for measuring the temperature of the gas as it flows between the sensors 62 and 63. Preferably, the temperature sensor 71 is a thermistor placed at substantially the center of the flow path 68. A temperature sensor lead 72 may extend along the flow path 68 to the transducer 62 and is connected to the microcomputer 65 and a second temperature sensor lead 73 may extend along the flow path 68 to the transducer 63 and is connected to the microcomputer 65.

In operation, the microcomputer 65 initially causes the ozone free reference gas, such as oxygen enriched feed gas, to be delivered to the flow path 68 and the flow path 68 is purged of ozone with the flow of feed gas. The microcomputer 65 then causes the drive circuit 64 to apply a high frequency electric pulse, for example, a single electric pulse having a frequency of about 40 kHz, to one of the transducers, for example, to transducer 62. The transducer 62 responds by emitting a sound pulse into the gas at one end of the flow path 68. At the same time, the microcomputer 65 starts a counter to count clock pulses until the receiver 67 detects that the sound pulse has reached the transducer 63. The clock pulse count and the temperature of the reference gas are stored in the microcomputer 65. A similar measurement is made by pulsing the transducer 63 and counting clock pulses until the receiver 66 detects that the transducer 62 has received the pulse. The two clock pulse time measurements are averaged to obtain a measurement of the time required for a high frequency sound pulse to travel through the feed gas for the predetermined distance between the transducers 62 and 63, without the influence of gas flow. The microcomputer 65 then causes ozone enriched output gas 69 from the ozone generator 61 to flow along the path 68 until all reference gas is purged from the path 68. Similar temperature and sound pulse travel time measurements in the flow direction and against the flow direction are made for the ozone containing output gas 69 and the times are averaged by the microcomputer 65. It will be appreciated that single measurements may be made for volumes of the reference gas and of the ozone containing gas in a closed chamber where gas flow is interrupted during the measurements. When gas flow is not a factor in the accuracy of the measurements, it is not necessary to average two measurements. Also, it will be appreciated that the temperature and sound pulse speed measurements for the feed gas may be stored and used over a period of time for calculating ozone concentration. New feed or reference gas measurements only need be taken when there is a possibility that they have changed from the original measurements. Generally, reference measurements every 5 to 10 minutes has been found to be acceptable.

For a binary gas, or a gas of N components with N–2 constraints, for example, a fixed ratio between two components, the concentration of a component, when measured ultrasonically, may be written as the equation $$P = \alpha/C^2 T + \beta T + \phi \qquad (1)$$

where P equals the concentration of the subject gas, C equals the timer counts for the ultrasonic pulse travel time over a predetermined distance in the gas, T equals the gas Kelvin temperature and $\alpha$, $\beta$ and $\phi$ are constants of the system. The first term of the equation is the temperature dependence of the speed of sound, while the second term corrects for slight temperature dependence of the piezoelectric transducer response. By determining the three constants in the equation through calibration, a two transducer sensor can be designed to directly measure the concentration of a gaseous component.

It has been found that a differential sensor may be made for measuring the concentration of a gas in a gaseous mixture when a reference gas stream is available which differs form the subject gas stream only by the absence of the subject gas. Thus, the ozone concentration from an ozone generator output may be easily and quite accurately determined by differential measurements with the ozone free feed gas. For the following description, a subscript "feed" is used for designating measurements and calculations relating to the ozone free feed gas 12 and a subscript "o" is used for designating measurements and calculations relating to the ozone containing output gas 13 in FIG. 7 thereof. The ozone concentration from the ozone generator may be indicated as $$P_o = -\alpha/(C_o)^2 T_o + \beta T_o + \phi \quad (2)$$

Similarly, the ozone concentration in the feed gas may be indicated as $$P_{feed} = -\alpha/(C_{feed})^2 T_{feed} + \beta T_{feed} + \phi \quad (3)$$

By subtracting equation (3) from equation (2), by observing that $P_{feed}$ is zero, by noting that $\beta T$ may be omitted since $\beta$ is normally small and that $T_o$ and $T_{feed}$ are similar, the ozone concentration from the ozone generator may be expressed as the equation $$P_o = -\alpha/(C_o)^2 T_o + \alpha/(C_{feed})^2 T_{feed} \quad (4)$$

$\Delta C$ may be defined as $(C_o - C_{feed})$ and $\Delta T$ may be defined as $(T_o - T_{feed})$. These definitions may be substituted into equation (4) to eliminate $C_o$ and $T_o$. Further, it may be observed that $\Delta C/C_{feed}$ and $\Delta T/T_{feed}$ will both be much smaller than 1. The resulting binomial expansion may be simplified by eliminating higher order terms to arrive at the equation $$P_o \approx -\alpha[2\Delta C/C_{feed} + \Delta T/T_{feed}] \quad (5)$$

With the equation (5), the ozone concentration may be easily related to the change in timer counts between the reference feed gas and the ozone enriched gas and to any temperature change in the gas at the sensor. The constant $\alpha$ may be determined by calibration, while $C_{feed}$ and $T_{feed}$ are measured for the reference feed gas. The differential mode of measurement using equation (5) is inherently more accurate than a direct measurement using equation (1). Direct measurement is subject to errors associated with violation of assumed constraints, e.g., in an oxygen sensor, variations of the oxygen/argon mix from the assumed naturally occurring ratio. Substitution of typical values for the terms eliminated in arriving at equation (5) indicate that an accuracy of a few tenths of a percent ozone is easily achievable. It should be appreciated that the differential method of measuring ozone concentration does not require measuring the oxygen concentration of the feed gas. Further, only occasional re-zeroing is necessary.

Once base measurements $C_{feed}$ and $T_{feed}$ are made for the feed gas and the sensor is then purged of the feed gas, updated ozone concentration calculations may be made, for example, at half-second intervals and the calculations may be smoothed by averaging, for example, the most recent ten readings.

It will be appreciated that various modifications and changes may be made to the above described preferred embodiment of an ozone concentration sensor without departing from the scope of the following claims.

We claim:

1. Apparatus for measuring the concentration of ozone produced by an ozone generator from an oxygen containing flow of substantially ozone free feed gas, said ozone generator having an output gas flow, said apparatus comprising sensor means for measuring the time required for a high frequency sound pulse to travel a predetermined distance through a volume of gas and for measuring the temperature of such volume of gas, programmed means for storing and processing pulse travel times and gas temperature measurements from said sensor means, means adapted for delivering the substantially ozone free feed gas to said sensor means whereby said sensor means measures a pulse travel time and a temperature for such feed gas, means adapted for delivering ozone containing output gas from the ozone generator to said sensor means whereby said sensor means measures a pulse travel time and a temperature for such output gas, and wherein said programmed means for storing and processing pulse travel time and gas temperature measurements from said sensor means includes means for determining the ozone concentration in such output gas from a calculated comparison made between the measured travel times and temperatures for such feed gas and such output gas, and wherein said programmed means determined the ozone concentration in such output gas using the equation $P_o = -\alpha [2\Delta C/C_{feed} + \Delta T/T_{feed}]$ wherein $P_o$ equals the ozone concentration in the output gas, $C_{feed}$ equals the feed gas pulse travel time, $T_{feed}$ equals the feed gas temperature, $\Delta C$ equals the difference between the feed gas and the output gas pulse travel times, $\Delta T$ equals the difference between the feed gas and the output gas temperatures and $\alpha$ is a constant.

2. Apparatus for measuring the concentration of ozone produced by an ozone generator from an oxygen containing flow of substantially ozone free feed gas, said ozone generator having an output gas flow, said apparatus comprising sensor means for measuring the time required for a high frequency sound pulse to travel a predetermined distance through a volume of gas and for measuring the temperature of such volume of gas, programmed means for storing and processing pulse travel times and gas temperature measurements from said sensor means, means adapted for delivering the substantially ozone free feed gas to said sensor means whereby said sensor means measures a pulse travel time and a temperature for such feed gas, means adapted for delivering ozone containing output gas from the ozone generator to said sensor means whereby said sensor means measures a pulse travel time and a temperature for such output gas, and wherein said programmed means for storing and processing pulse travel time and gas temperature measurements from said sensor means includes means for determining the ozone concentration in such output gas from a calculated comparison made between the measured travel times and temperatures for such feed gas and such output gas, wherein said sensor means is connected to receive output gas from the ozone generator, and wherein said means adapted to deliver feed gas to said sensor means further includes means for interrupting the generation of ozone by the ozone generator whereby the feed gas flows through the ozone generator and flows from the ozone generator output to said sensor means unchanged in composition.

3. Apparatus for measuring the concentration of ozone produced by an ozone generator, as set forth in claim 2, and wherein said means adapted for delivering feed gas and said means adapted for delivering output gas includes at least one valve controlled by said programmed means.

4. A method for measuring the ozone concentration in the output gas from an ozone generator which converts at least some oxygen in a substantially ozone free feed gas into ozone while said ozone generator is powered-up and operated in a turned-on, controlled condition sufficient to excite said some oxygen, said method comprising the steps of:

a) measuring the temperature of the feed gas and measuring the time that it takes a sound pulse to travel a predetermined distance in the feed gas, said measurements being made in the output gas from said ozone generator while said ozone generator is in a turned-off condition wherein said some oxygen is not excited;

b) measuring the temperature of the output gas and measuring the time that it takes a sound pulse to travel said predetermined distance in the output gas while said ozone generator is powered-up and operated in a turned-on condition wherein said some oxygen is excited and c) determining the ozone concentration in the output gas from comparisons and calculations made between the stored data of said temperature and pulse travel time measurements for both the feed gas and the output gas when said some oxygen is excited.

5. A method for measuring the ozone concentration in the output gas from an ozone generator, as set forth in claim 4, and wherein the ozone concentration in the output gas is determined according to the formula $P_o = -\alpha[2\Delta C/C_{feed} + \Delta T/T_{feed}]$ wherein $P_o$ equals the output gas ozone concentration with the ozone generator on, $C_{feed}$ equals the ozone generator off output gas pulse travel time, $T_{feed}$ equals the ozone generator off output gas temperature, $\Delta C$ equals the difference between the ozone generator off and the ozone generator on output gas pulse travel times, $\Delta T$ equals the difference between the ozone generator off and the ozone generator on output gas temperatures and $\alpha$ is a constant.

6. A method for measuring the ozone concentration in the output gas from an ozone generator, as set forth in claim 4, and wherein the ozone concentration in the output gas is determined according to the formula $P_o = -\alpha[2\Delta C/C_{feed} + \Delta T/T_{feed}]$ wherein $P_o$ equals the output gas ozone concentration, $C_{feed}$ equals the feed gas pulse travel time, $T_{feed}$ equals the feed gas temperature, $\Delta C$ equals the difference between the feed gas and the output gas pulse travel times, $\Delta T$ equals the difference between the feed gas and the output gas temperatures and $\alpha$ is a constant.

7. A system for producing an ozone containing gas and for measuring the ozone concentration in said produced gas comprising, in combination, oxygen concentrator means for establishing a flow of oxygen enriched gas from air, ozone generator means for converting a portion of the oxygen in such oxygen enriched gas flow into a flow of ozone enriched gas, sensor means for measuring the temperature of a gas sample and for measuring the time for a sound pulse to travel a predetermined distance in such gas sample, means for selectively delivering flows of the oxygen enriched gas and of the ozone enriched gas to said sensor means including means for delivering a flow of output gas from said ozone generator means to said sensor means means for interrupting operation of said ozone generator means, whereby the oxygen enriched gas passes through said ozone generator means to said sensor means unchanged, and microprocessor means for controlling the flows of oxygen enriched gas and of ozone enriched gas to said sensor means and for determining the ozone concentration in said ozone enriched gas from time and temperature measurements for said oxygen enriched gas and said ozone enriched gas.

8. A system for producing an ozone containing gas and for measuring the ozone concentration in said produced gas comprising, in combination, oxygen concentrator means for establishing a flow of oxygen enriched gas from air, ozone generator means for converting a portion of the oxygen in such oxygen enriched gas flow into a flow of ozone enriched gas, sensor means for measuring the temperature of a gas sample and for measuring the time for a sound pulse to travel a predetermined distance in such gas sample, means for selectively delivering flows of the oxygen enriched gas and of the ozone enriched gas to said sensor means, microprocessor means for controlling the flows of oxygen enriched gas and of ozone enriched gas to said sensor means and for determining the ozone concentration in said ozone enriched gas from time and temperature measurements for said oxygen enriched gas and said ozone enriched gas, and an accumulator adapted for storing ozone output gas from said ozone generator means so as to enable a more steady state flow condition of ozone gas through said system during said ozone generation interruption operation for concentration measurement of the oxygen enriched gas.

9. A system for producing an ozone containing gas and for measuring the ozone concentration in said produced gas comprising, in combination, oxygen concentrator means for establishing a flow of oxygen enriched gas from air, ozone generator means for converting a portion of the oxygen in such oxygen enriched gas flow into a flow of ozone enriched gas, sensor means for measuring the temperature of a gas sample and for measuring the time for a sound pulse to travel a predetermined distance in such gas sample, means for selectively delivering flows of the oxygen enriched gas and of the ozone enriched gas to said sensor means including a first valve adapted to deliver oxygen enriched gas to said sensor means, a second valve adapted to deliver ozone enriched gas to said sensor means, means for maintaining a predetermined back pressure in gas flowing through said sensor means, microprocessor means controlling operation of said first and second valves for selectively controlling the flows of oxygen enriched gas and of ozone enriched gas to said sensor means and for determining the ozone concentration in said ozone enriched gas from time and temperature measurements for said oxygen enriched gas and said ozone enriched gas.

* * * * *